United States Patent
Kitamura

(10) Patent No.: US 6,404,205 B1
(45) Date of Patent: Jun. 11, 2002

(54) METHOD FOR TESTING THE RELIABILITY OF AN ELECTROCHEMICAL GAS SENSOR

(75) Inventor: Naoya Kitamura, Kyoto (JP)

(73) Assignee: Japan Storage Battery Co., Ltd., Kyoto (JP)

( * ) Notice: Subject to any disclaimer, the term of this patent is extended or adjusted under 35 U.S.C. 154(b) by 0 days.

(21) Appl. No.: 09/530,906

(22) PCT Filed: Sep. 9, 1998

(86) PCT No.: PCT/JP98/04044

§ 371 (c)(1),
(2), (4) Date: May 8, 2000

(87) PCT Pub. No.: WO00/14524

PCT Pub. Date: Mar. 16, 2000

(30) Foreign Application Priority Data

May 9, 1997 (JP) .............................................. 9-135975

(51) Int. Cl.[7] .......................... G01N 27/62; G01N 27/26
(52) U.S. Cl. ........................ 324/464; 324/465; 324/468; 204/424; 204/431; 73/23.1
(58) Field of Search ................................ 324/464, 465, 324/468; 204/425, 426, 429, 424, 428, 427; 422/94; 73/1.06, 23.2; 205/779.5

(56) References Cited

U.S. PATENT DOCUMENTS

| | | | | |
|---|---|---|---|---|
| 3,787,308 A | * | 1/1974 | Malaspina et al. | 204/432 |
| 4,021,326 A | * | 5/1977 | Pollner et al. | 204/429 |
| 4,107,019 A | * | 8/1978 | Takao et al. | 204/425 |
| 4,123,131 A | * | 10/1978 | Pearce, Jr. et al. | 439/206 |
| 4,126,532 A | * | 11/1978 | Takao et al. | 204/426 |
| 4,151,739 A | * | 5/1979 | Breuer et al. | 73/1.06 |
| 4,171,253 A | * | 10/1979 | Nolan et al. | 204/411 |
| 4,207,159 A | * | 6/1980 | Kimura et al. | 204/425 |
| 4,224,113 A | * | 9/1980 | Kimura et al. | 205/784.5 |
| 4,265,714 A | * | 5/1981 | Nolan et al. | 205/779.5 |
| 4,267,030 A | * | 5/1981 | Breuer et al. | 204/278 |
| 4,399,017 A | * | 8/1983 | Inoue et al. | 204/425 |
| 4,569,748 A | * | 2/1986 | Yamakawa et al. | 204/429 |

(List continued on next page.)

FOREIGN PATENT DOCUMENTS

| | | | |
|---|---|---|---|
| EP | 0 039 549 A2 | 11/1981 | .......... G01N/27/46 |
| JP | 58-143262 | 8/1983 | .......... G01N/27/46 |
| JP | 4-190154 | 7/1992 | .......... G01N/27/416 |
| JP | 7-504973 | 6/1995 | .......... G01N/27/416 |
| WO | 98/25139 | 6/1998 | .......... G01N/33/00 |

OTHER PUBLICATIONS

Japanese Abstract No. 10311815, dated Nov. 24, 1998.
International Search Report Dec. 15, 1998.

*Primary Examiner*—N. Le
*Assistant Examiner*—Wasseem H. Hamdan
(74) *Attorney, Agent, or Firm*—Sughrue Mion, PLLC

(57) ABSTRACT

The present invention is a method by which the deterioration judgement and the correction of an electrochemical carbon monoxide gas sensor are simply carried out without using the correction gas. The method of the present invention is that: the voltage is applied from the outside so that the working electrode of the electrochemical carbon monoxide gas sensor is operated as the negative electrode, and the counter electrode is operated as the positive electrode, and hydrogen is generated from the working electrode, and oxygen is generated from the counter electrode; after that, the potential of the working electrode and the counter electrode is returned to the operation potential as the sensor; and by using the reaction on the hydrogen remained in the vicinity of the working electrode, the sensor current is generated, thereby, it is tested whether the sensor is normally operated.

9 Claims, 6 Drawing Sheets

U.S. PATENT DOCUMENTS

| | | | | |
|---|---|---|---|---|
| 5,273,640 A | * | 12/1993 | Kusanagi et al. | 204/401 |
| 5,403,452 A | * | 4/1995 | Hielscher et al. | 205/781 |
| 5,573,648 A | * | 11/1996 | Shen et al. | 204/412 |
| 5,573,650 A | * | 11/1996 | Fukaya et al. | 204/424 |
| 5,668,302 A | * | 9/1997 | Finbow et al. | 73/23.2 |
| 5,698,084 A | * | 12/1997 | Weyl et al. | 204/424 |
| 5,716,506 A | * | 2/1998 | Maclay et al. | 204/424 |
| 5,841,021 A | * | 11/1998 | De Castro et al. | 73/23.2 |
| 5,865,973 A | * | 2/1999 | Kiesele et al. | 204/415 |
| 6,074,539 A | * | 6/2000 | Deininger et al. | 204/412 |
| 6,165,347 A | * | 12/2000 | Warburton | 205/782.5 |
| 6,222,372 B1 | * | 4/2001 | Fukaya et al. | 324/464 |

* cited by examiner

METHOD FOR TESTING THE RELIABILITY OF AN ELECTROCHEMICAL GAS SENSOR

TECHNICAL FIELD

The present invention relates to a testing method of an electrochemical gas sensor used for measuring the component concentration of a carbon monoxide gas. In more detail, the present invention relates to a testing method for judging an operation condition of an electrochemical gas sensor for use in a gas alarm unit which is ordinarily provided in a ship or manhole, tunnel or home, and widely used for the prevention of poisoning accidents, caused by the blowout gas or the exhaust gas of a heater or car, the early detection of the fire, the prevention of fire caused by explosion, and the like.

BACKGROUND TECHNOLOGY

The electrochemical gas sensor is a sensor which introduces the gas component to be detected onto a working electrode having a catalytic action through a membrane, and outputs the voltage or current corresponding to the gas concentration by oxidizing or reducing the gas, and because the sensor has a small size and light weight, and operates under the normal temperature and normal pressure, and is highly reliable and relatively low cost, it is widely used for the poisoning alarm unit or the industrial measuring unit, and the like.

Conventionally, a general structure of the widely and practically used electrochemical gas sensor is as shown in FIG. 1. Further, a general electric circuit which electrically drives such the electrochemical gas sensor, and by which the output is obtained, is shown in FIG. 2. According to FIG. 2, the principle of operation of the electrochemical gas sensor will be described.

The sensor has the structure in which a synthetic resin holder (9), and oxygen permeable film pressing member (6), membrane pressing member (14) are used, and the gas permeable membrane (12), working electrode (11), counter electrode (8), reference electrode (13), electrolyte holding member (10), and lead wires (1), (2) and (4) to make electrical conduction to each electrode are arranged, and the electrolyte (7) is hermetically sealed inside. The electrode is the catalyst whose main component is the precious metals such as platinum or platinum black, and by which the gas having the reduction action such as carbon monoxide, hydrogen, or the like, or the gas having the oxidation action is effectively oxidized or reduced on the working electrode (11).

The potential of the working electrode (11) is held at a suitable value for the oxidation and reduction response of the gas to the reference electrode (13) by the external circuit shown in FIG. 2. In this case, the current is not circulated to and from the reference electrode which is the reference of the potential, and which only regulates the potential of the working electrode and has no relation to the reaction.

Further, because the potential of the counter electrode is not regulated, the potential of the counter electrode is the natural electrode potential for the reaction corresponding to the reaction on the working electrode. Accordingly, the oxidation and reduction reaction of the gas to be measured occurs only on the working electrode, and the reaction of the other side occurs only on the counter electrode.

When the gas to be measured is diffused from the outside in the permeable membrane (12) and reaches the working electrode (11), the oxidation reaction shown in the relational expression (A) occurs. On the one hand, simultaneously, on the counter electrode (8) through the electrolyte (7), the reduction reaction of the oxygen shown in the relational expression (B) occurs. The oxygen diffuses in the oxygen permeable membrane (5) from the atmosphere in which the sensor is used, and is dissolved in the electrolyte (7), and diffused in the electrolyte and reaches the counter electrode (8).

(Working electrode reaction) $CO+H_2O \rightarrow CO_2+2H^++2e^-$     (A)

(Counter electrode reaction) $1/2O_2+2H^++2e^- \rightarrow H_2O$     (B)

(Total reaction) $CO+1/2O_2 \rightarrow CO_2$     (C)

At this time, the current flows between the working electrode and the counter electrode is shown by the relational expression (D), and is proportional to the concentration of the gas to be measured; therefore, by leading the current through the lead wire (4) connected to the working electrode and the lead wire (2) connected to the counter electrode to the outside, the concentration of the gas to be measured can be detected.

(the relationship of the reaction current and gas concentration)

$$i = \frac{F \times A \times D \times C}{\sigma} \times n \quad (D)$$

Where:
- i: reaction current
- F: Faraday constant
- A: area of the diffusion surface
- D: diffusion coefficient of the gas
- C: concentration of the gas
- σ: thickness of the diffusion layer
- n: number of reaction electrons (in the reaction of the sensor, F, A, D, σ, n are constant)

In the case of the reaction, concerning the water ($H_2O$) consumed on the working electrode by the oxidation of the carbon monoxide gas, because the amount of the equivalent is generated by the reduction of the oxygen ($O_2$) in the outside air on the counter electrode, there is no chemically consumed component.

However, in the practical use, there is a case in which the sensor is not operated normally, by the extrinsic factors such as the aging deterioration of members constituting the sensor or the contact continuity condition, or the stain of the membrane through which the gas diffuses and penetrates.

Accordingly, when ordinarily, the poisoning alarm unit or the measuring device using such the electrochemical carbon monoxide gas sensor is used, the inspection or correction of the sensor output is necessary before using, and when the use is for a long period of time even in the continuous use, it is necessary that the measurement is periodically stopped for the correction or replacement of the sensor so that the accuracy or reliability is maintained. Conventionally, the correction of the sensor is conducted in such a manner that the maintenance man or the user himself flows the correction gas including a predetermined concentration carbon monoxide into the sensor and the sensor output generated at the time is measured. However, it is very troublesome to conduct such the correction operation periodically, and there is a possibility that the correction operator is exposed to the carbon monoxide gas for correction.

Further, due to such difficulties, the periodical inspection may not be conducted, and thus, in the case where the concentration of the carbon monoxide of the atmosphere is increased, and a possibility of poisoning occurs, the sensor may not normally operate, and the alarm may not be provided accordingly.

DISCLOSURE OF THE INVENTION

The present invention is described in the following (1) to (9).

(1) A testing method of an electrochemical gas sensor, in which: a working electrode which electrochemically oxidizes or reduces the first gas component to be detected, a counter electrode which acts electrochemical reduction reaction or oxidation reaction corresponding to an oxidized or reduced amount of the first gas component, and an electrolyte are provided; and an sensor output which is a value of the oxidation current or reduction current of the first gas component, is calculated and the concentration of the first gas component is detected, the testing method of an electrochemical gas sensor, which includes the steps of that: in which the voltage in which the current flows in the reverse direction to the oxidation current or reduction current of the first gas component, is applied between the working electrode and the counter electrode from the outside; and after the second gas component is generated on the working electrode so as to be a predetermined concentration by the electrolysis of the electrolyte, the sensor output which is a value of the oxidation current or reduction current on the working electrode of the second gas component, is measured, and in which the second gas component shows a sensor at output practically proportional to the sensor output of the first gas component in the concentration corresponding to the concentration of the first gas component.

(2) The testing method of an electrochemical gas sensor described in (1), in which the sensor is tested by using a correction value which is a ratio of the output of the measuring sensor in the predetermined concentration of the second gas component, and the sensor output calculated according to the known reference from the predetermined concentration of the second gas component.

(3) The testing method of an electrochemical gas sensor described in (1), in which the sensor is tested by using a correction value which is a ratio of the second gas component concentration calculated according to the known reference from the measuring sensor output, and the predetermined concentration of the second gas component.

(4) The testing method of an electrochemical gas sensor described in (1), in which the first gas component is carbon monoxide.

(5) The testing method of an electrochemical gas sensor described in (4), in which the electrolyte is an aqueous solution, and the second gas component is hydrogen.

(6) The testing method of an electrochemical gas sensor, in which the testing is correction, and/or deterioration judgement, and/or life judgement.

(7) An electrochemical gas sensor, in which a testing means according to the testing method described in (6), is provided.

(8) An apparatus which is provided with an electrochemical gas sensor, and a testing means according to the testing method described in (6).

(9) A control apparatus of the electrochemical gas sensor which is provided with a testing means according to the testing method described in (4).

As described above, at the time of the correction of an electrochemical carbon monoxide gas sensor, the present invention judges the deterioration of the sensor by means of temporarily operating the electrode potential by the outside, and generating the gas having the same action as at the time when the correction gas flows, on the electrode, and then, returning the potential to the normal potential, and by the reaction of the sensor upon the generated and remained gas, and can correct the sensor, without practically using the correction gas including carbon monoxide.

Figure 1:
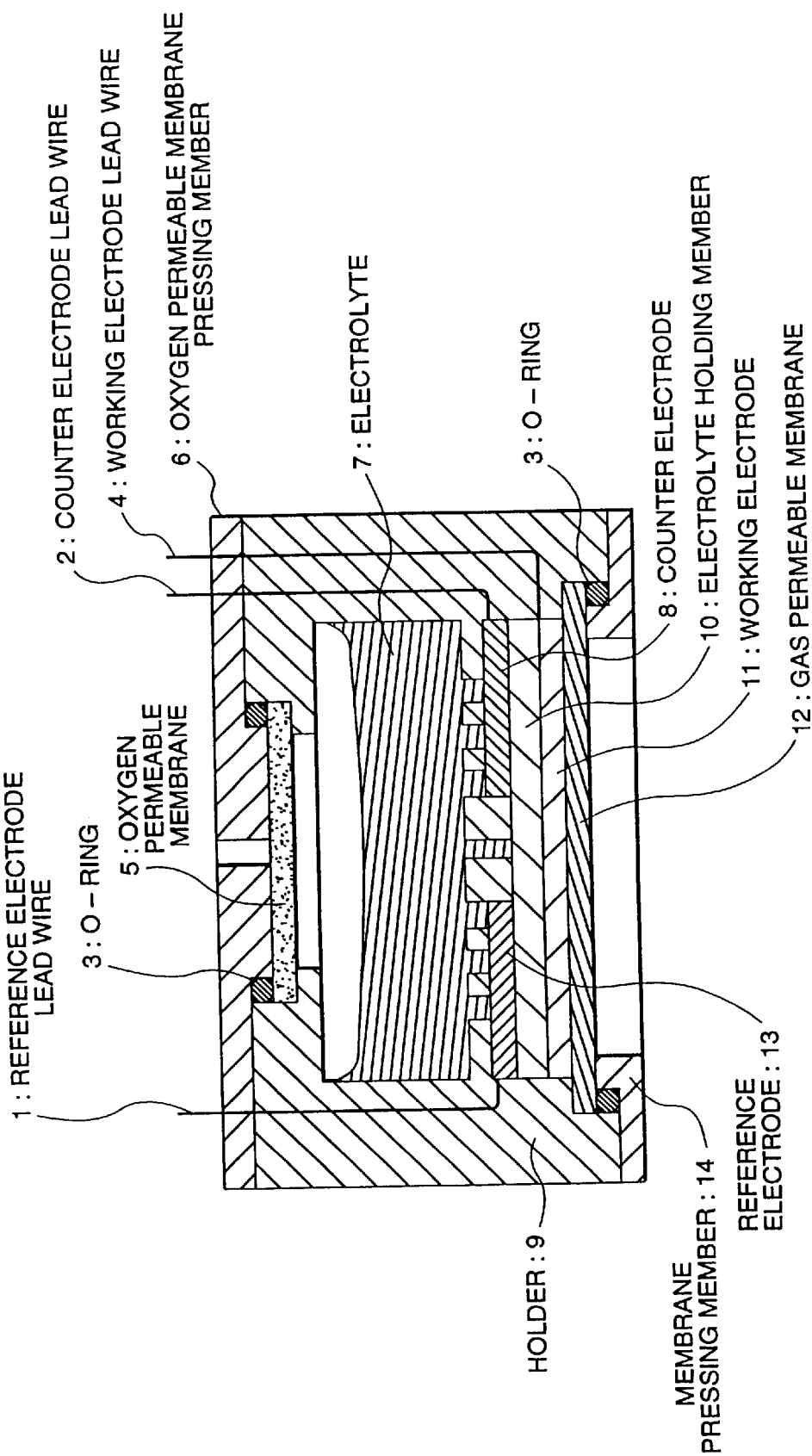
FIG. 1 is a view showing a structural section of an electrochemical carbon monoxide gas sensor.

Incidentally, in the drawings, numeral 1 is a reference electrode lead wire, numeral 2 is a counter electrode lead wire, numeral 3 is an O-ring, numeral 4 is a working electrode lead wire, numeral 5 is an oxygen permeable membrane, numeral 6 is an oxygen permeable membrane pressing member, numeral 7 is an electrolyte, numeral 8 is a counter electrode, numeral 9 is a holder, numeral 10 is an electrolyte holding member, numeral 11 is a working electrode, numeral 12 is a gas permeable membrane, numeral 13 is a reference electrode, and numeral 14 is a membrane pressing member.

BEST MODE FOR CARRYING OUT THE INVENTION

Hereinafter, an embodiment of the present invention will be described.

An electrochemical carbon monoxide gas sensor oxidizes carbon monoxide and reduces oxygen by using a catalytic electrode, and the current due to the reaction is used as a detection means of the gas concentration, and the catalytic electrode is effective not only for the carbon monoxide, but also for other reactive gases.

For example, in the case of a sensor in which platinum black, whose catalytic action is very strong, is used for the electrode, also when hydrogen is supplied onto the working electrode instead of carbon monoxide, the following reaction occurs and the sensor current is generated.

(Working electrode reaction) $H_2 \rightarrow 2H^+ + 2e^-$     (F)

(Counter electrode reaction) $1/2O_2 + 2H^+ + 2e^- \rightarrow H_2O$     (G)

(Total Reaction) $H_2 + 1/2O_2 \rightarrow H_2O$     (H)

Also in this case, because the principle of operation of the sensor is the same as in the case of carbon monoxide gas, the sensor is not normally operated, due to the external factors such as the aging deterioration of members constituting the sensor or the electrical contact continuity condition, or stains of the membrane through which the gas diffuses or penetrates, or the like.

Further, as widely known, when the constant voltage is applied between 2 precious metal electrodes in the solution electrolyte, the electrolysis of water occurs by the following reaction formulas, and hydrogen is generated from one electrode (negative electrode) and oxygen is generated from the other electrode (positive electrode).

(Negative electrode reaction) $2H^+ + 2e^- \rightarrow H_2$      (F)

(Positive electrode reaction) $H_2O \rightarrow 1/2 O_2 + 2H^+ + 2e^-$      (G)

(Total reaction) $H_2O \rightarrow H_2 + 1/2 O_2$      (H)

Accordingly, when the constant voltage is applied from the outside so that the working electrode is operated as the negative electrode, and the counter electrode is operated as the positive electrode, hydrogen is generated from the working electrode, and oxygen is generated from the counter electrode. After that, when the potential of the working electrode and the counter electrode is returned to the operation potential as the sensor, it reacts on the hydrogen remained in the vicinity of the working electrode, and the sensor current is generated.

Because this reaction on the hydrogen is the same as the reaction on the carbon monoxide, when the difference from the reference value is extremely large by the comparison of the sensor current at that time to the previously obtained reference value, it shows that the degree of the deterioration of the carbon monoxide sensor is large, and when the difference is small, it shows that the degree of the deterioration is small.

Accordingly, whether the sensor is normally operated for the carbon monoxide, can be greatly easily and simply tested and detected.

The reference sensor output means a sensor output when concretely, the carbon monoxide gas sensor is used, and the electrolyte water is subjected to the electrolysis for a predetermined time, and hydrogen is generated and remained for a predetermined time, and it may be a previously made value, or a value measured at the same hydrogen generation time and remained time, before the deterioration judgement time or the measurement at the time of correction.

Further, it may be compared, while periodically obtaining the sensor output as described above, with the relationship of the before and after. On the one hand, the reference hydrogen concentration means the hydrogen concentration in which the sensor output is converted by the calibration curve, and the like. In addition to that, in the comparison, at least 2 points of the reference value and the measuring value are necessary. Therefore, it may be judged by using multipoints.

When water is electrolyzed, the concentration of hydrogen generated on the working electrode is 100%, and is very thick as compared to the concentration of hydrogen corresponding to 10 to 1,000 ppm which is the concentration of carbon monoxide as an object of the normal measurement, however, when the time to electrolyze water is reduced to a short time, and the measurement is conducted after the passage of an appropriate time, a large part of the hydrogen diffuses into the outside air, and an appropriate amount of hydrogen remains in the vicinity of the electrode, therefore, there is no problem. Further, although water in the electrolyte is consumed by the electrolysis of water, when the time to electrolyze water is reduced to a short time, because the consumed amount of the water is very small, there is no problem for the function of the sensor.

Further, in the case where it is disadvantageous to the measurement of the concentration of carbon monoxide that interference of the sensitivity by hydrogen occurs, there are cases in which the hydrogen is selectively reacted and removed by using catalysis such as ruthenium which selectively reacts on the hydrogen, on the front stage of the gas introducing portion of the sensor, or the hydrogen is selectively removed by using the difference of the rate of absorption of hydrogen and carbon monoxide, by using the absorbent such as activated carbon, zeolite, or the like, in the same manner, on the front stage of the gas introducing portion of the sensor, however, because the method of the present invention directly uses the reaction acted on the working electrode, the method is not influenced by the means arranged on the front stage portion of the sensor.

EXAMPLES

As an example which preferably realizes the effect of the present invention, an electrochemical carbon monoxide sensor having the structure in FIG. 1 is made on an experimental basis, and the effect is confirmed.

The working electrode, counter electrode and reference electrode are made by heating and press-fitting the kneaded material of water suspension of water and ethylene tetra fluoride polymer (made by Mitsui phloro-chemical Co. Trade name is 30-J) onto the stainless plate which is made mesh-like, and on which platinum black is used as catalyst.

Platinum is used for each lead wire. For gas permeable membrane, 0.3 mm thick porous fluororesin (made by Sumitomo Denko Co., trade name: Phloro-pore FY-050), and for oxygen permeable membrane, 0.1 mm thick porous fluororesin film (made by Nitto Denko Co. trade name: NTF-1122) are used by being punched out to the predetermined shape.

Figure 2:
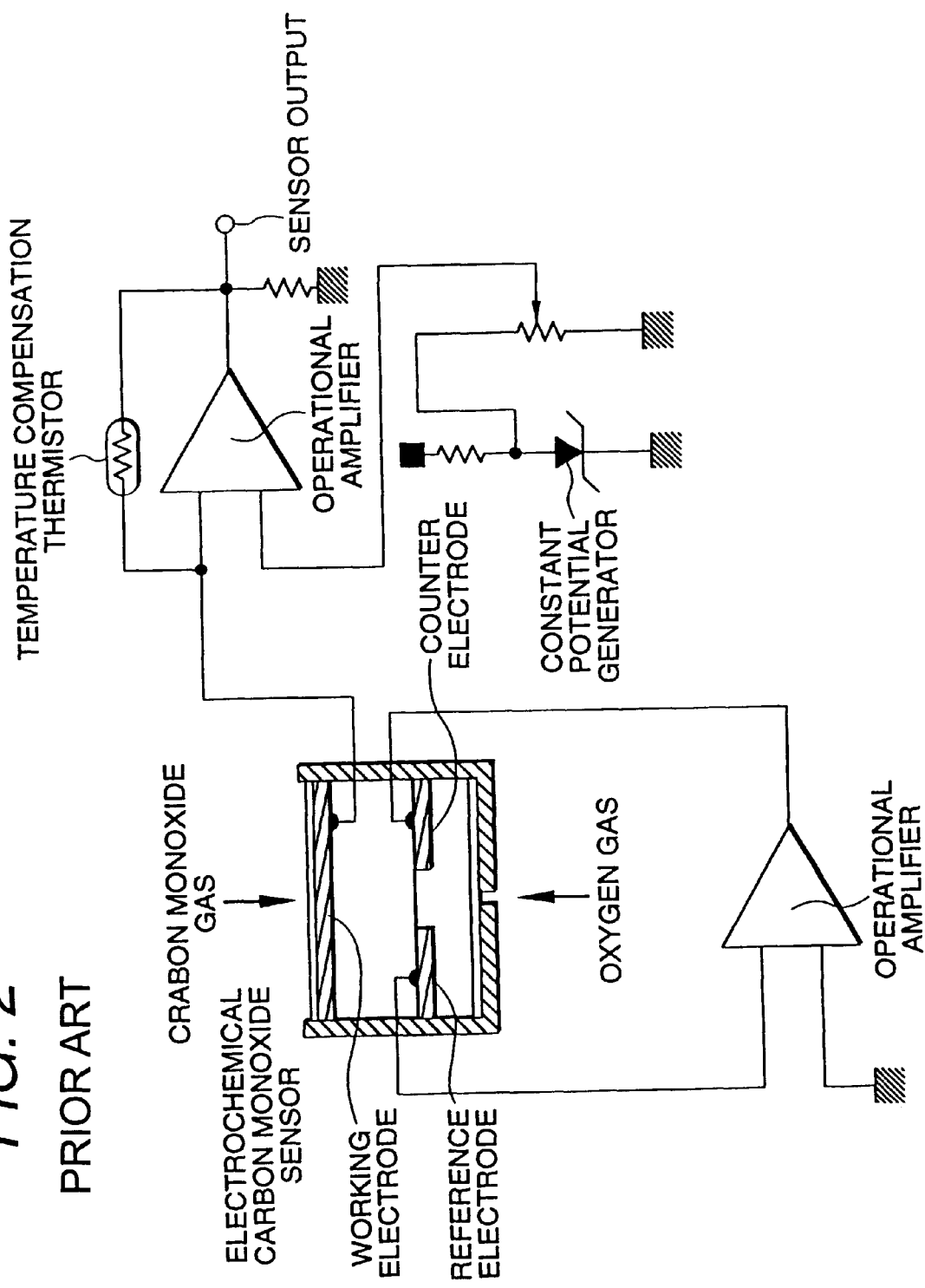
FIG. 2 is a view showing an electric circuit for the drive and output of the electrochemical carbon monoxide gas sensor.

For the electrolyte, sulfuric acid of 6 mol/L concentration is used. The potential of the working electrode and counter electrode is set by using the constant potential generator (made by Hokuto Denko Co. trade name: Potentiostat) as a unit which can perform the role of the operational amplifier in FIG. 2, and by using the potential of the reference electrode as the reference, the potential of the working electrode is set, and the sensor output is measured.

In order to check that hydrogen gas is effective as the correction or deterioration judgement gas, the reaction of the sensor on the carbon monoxide and the reaction on the hydrogen are investigated. The result of this is shown in FIG. 3.

Figure 3:
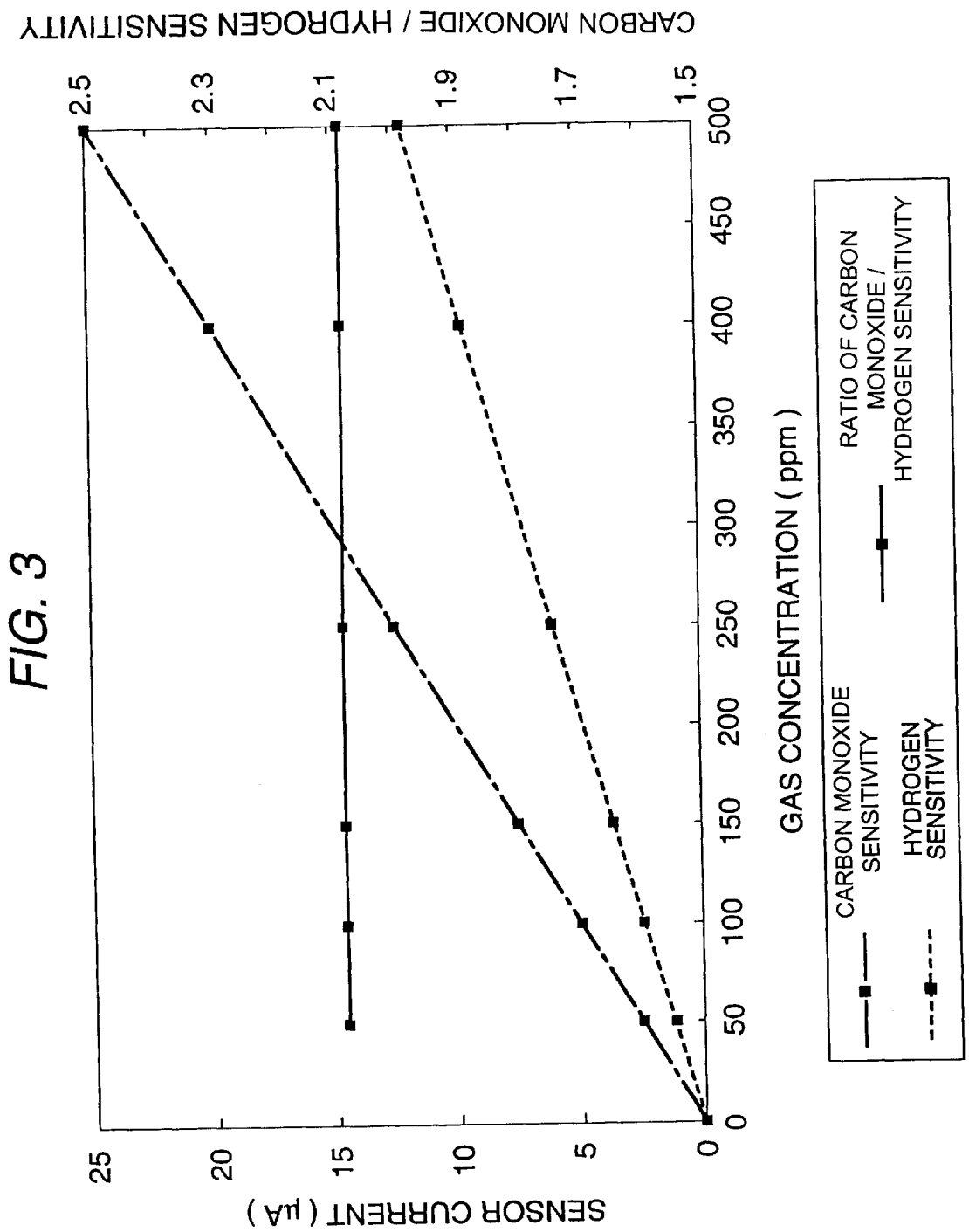
FIG. 3 is a view showing a result in which the reaction characteristics of the electrochemical carbon monoxide gas sensor are practically measured, in order to show the action and the effect of the present invention.

In FIG. 3, the sensor output current to the various concentration of the carbon monoxide and hydrogen, and the ratio of the output to the carbon monoxide and the output to the hydrogen are shown, and the characteristics of the reaction of the sensor shows the same inclination to both of them although there is a difference of outputs between them, and the ratio of the output is a constant value without depending on the concentration.

Accordingly, in the normal measurement range, the sensor output by the carbon monoxide has the relationship of 1 to 1 to the output by the hydrogen, and because, by the output value to either one gas, the concentration of the other gas can be known, it is confirmed that the hydrogen gas is effective as the correction or/and deterioration judgement gas of the electrochemical carbon monoxide sensor.

Next, in order to investigate that hydrogen gas is effective as the correction or deterioration judgement gas, even when the sensor is abnormal, out of the normal measurement range, the sensor in which the fouling condition is reproduced such that water drops are intentionally put on a portion of the gas permeable membrane, and the sensor in which the condition that the catalyst capability is deteriorated, is reproduced by decreasing the amount of the catalyst which is press-fitted onto the working electrode, are respectively made on an experimental basis, and their characteristics are investigated.

Figure 4:
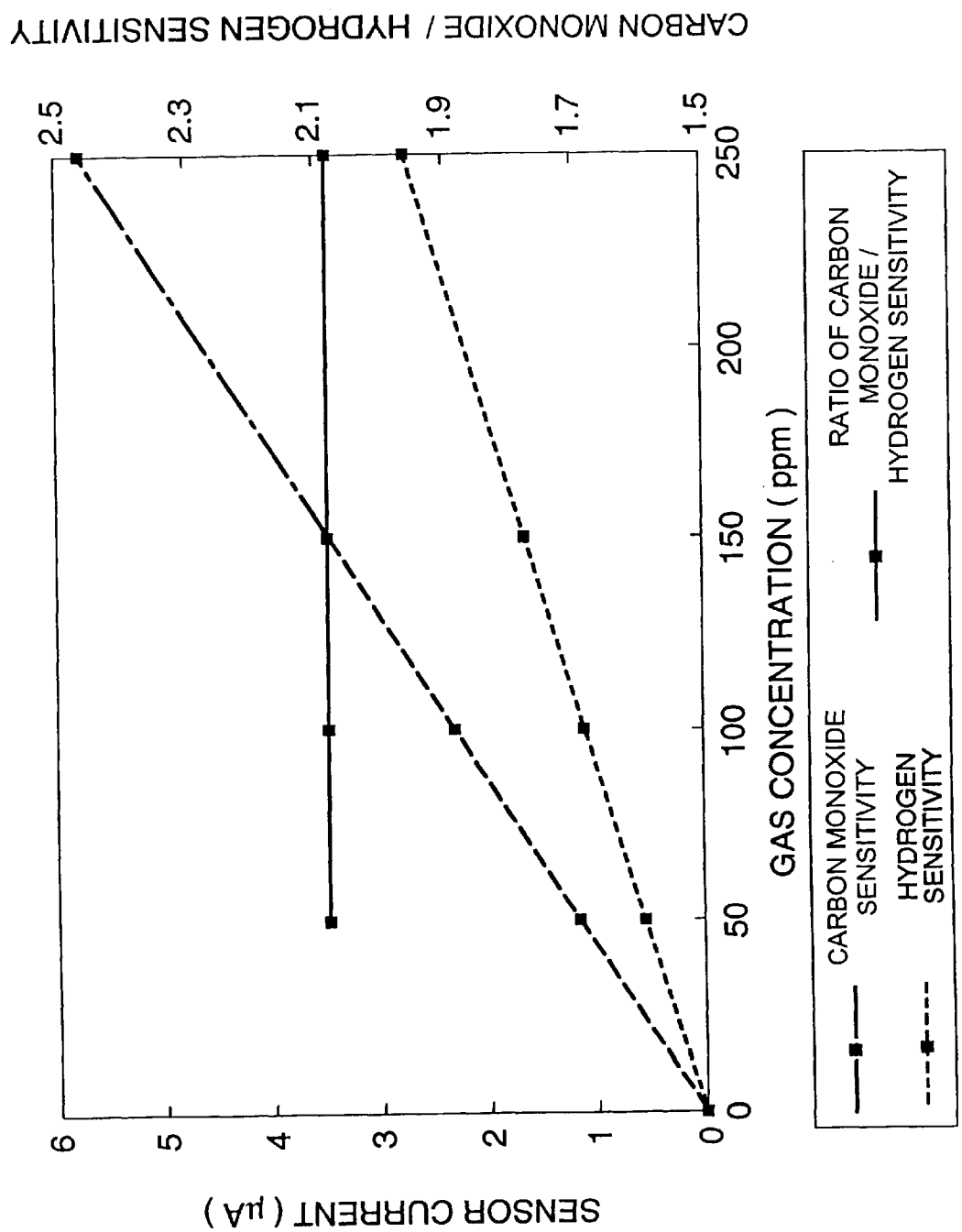
FIG. 4 is a view showing a result in which the reaction characteristics of the electrochemical carbon monoxide gas sensor, whose membrane section is stained, are practically measured, in order to show the action and the effect of the present invention.
Figure 5:
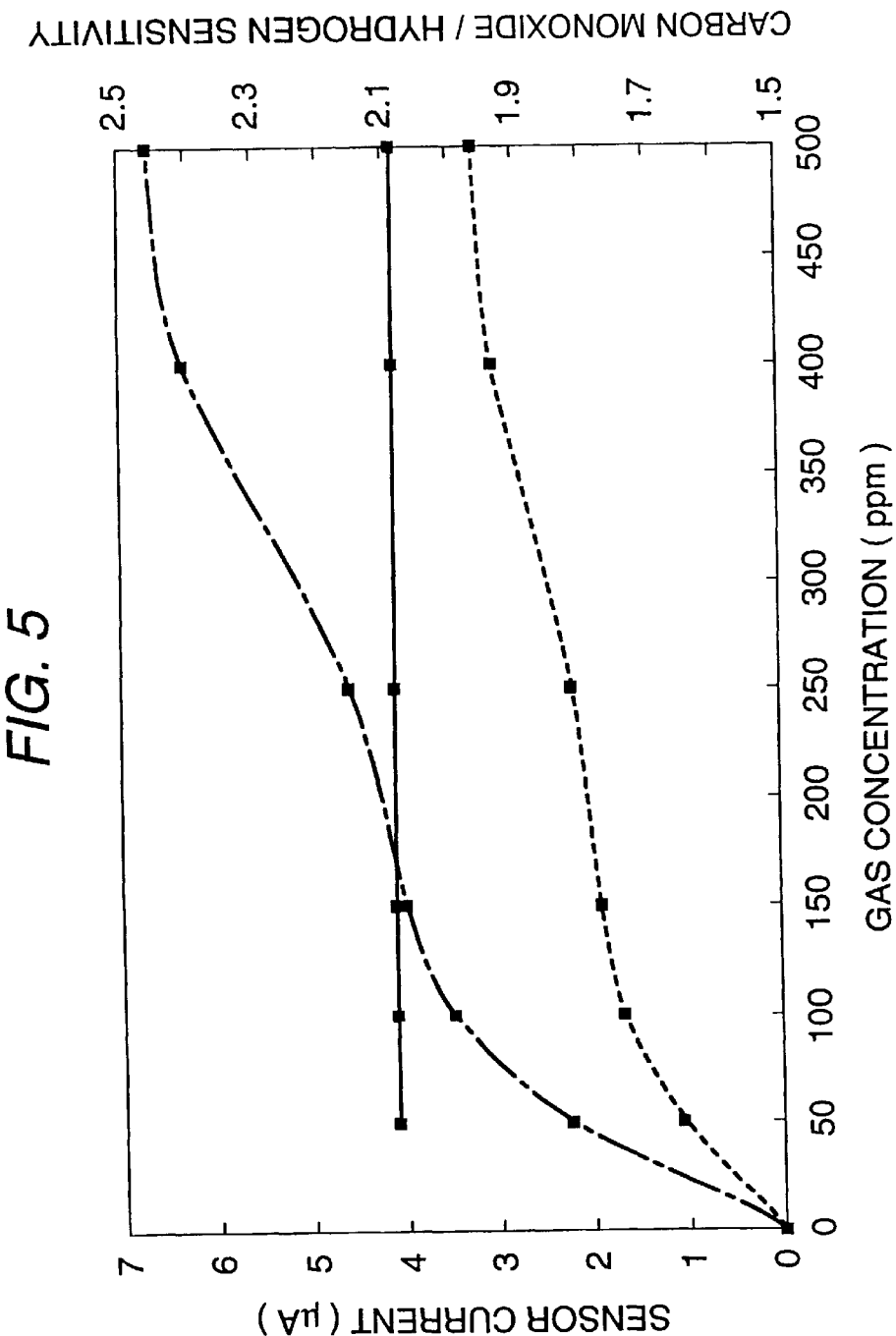
FIG. 5 is a view showing a result in which the reaction characteristics of the electrochemical carbon monoxide gas sensor, in which an amount of the catalyst of the electrode is decreased, are practically measured, in order to show the action and the effect of the present invention.

The measurement result of the output characteristics of the sensor whose gas permeable membrane is fouled, is shown in FIG. 4, and the measurement result of the output characteristics of the sensor whose catalysis amount is decreased, is shown FIG. 5. In any case of FIG. 4 and FIG. 5, in the same manner as in the result in FIG. 3, the ratio of the outputs is constant without depending on the concentration.

From the result of the experiments shown in FIG. 3, FIG. 4 and FIG. 5, not only in the normal measurement range, but also in the abnormal case, the sensor output by the carbon monoxide has the relationship of 1 to 1 to the output by the hydrogen, and because, by the output value to either one gas, the concentration of the other gas can be known, the hydrogen gas is effective as the correction or/and deterioration judgement gas of the electrochemical carbon monoxide sensor.

In order to verify the condition of generation of hydrogen by the electrolysis of water in this sensor, the potential of the working electrode is scanned with respect to the reference electrode, and the change of the current value at that time is checked. The result of this is shown in FIG. 6.

Figure 6:
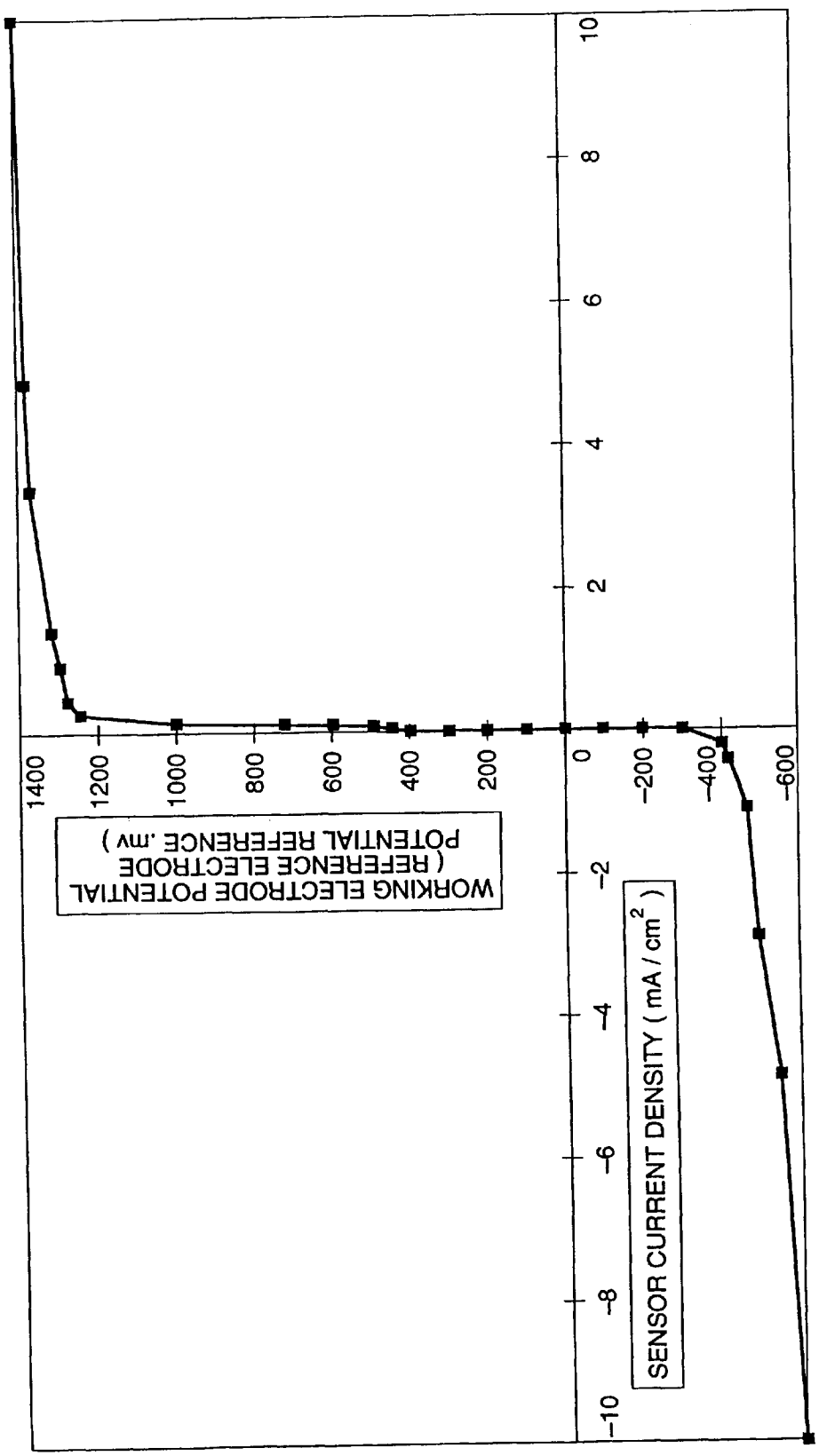
FIG. 6 is a view showing a result in which the current-voltage characteristics of the electrochemical carbon monoxide gas sensor are practically measured, in order to show the action and the effect of the present invention.

In FIG. 6, the axis of ordinate shows the potential of the working electrode using the reference electrode as the reference (0 V). Further, the reaction of the other side of the reaction of the working electrode occurs on the counter electrode. In this case, in the positive side of the axis of ordinate, the working electrode acts the positive electrode, that is, the side of generation of oxygen, and in the negative side, the working electrode acts as the negative electrode, that is, the side of generation of hydrogen. The theoretical decomposition voltage of water is, as well known, 1.23 V.

In the practical reaction, the over-voltage is generated according to the nature of the electrode, and generation voltage of hydrogen and oxygen is higher than the theoretical voltage, and in the case of the sensor, from FIG. 6, it is found that, because of rapid increase of the current value, the generation of oxygen occurs from the vicinity in which the voltage difference from the reference electrode exceeds 1200 mV, and the generation of hydrogen occurs from the vicinity in which the voltage difference from the reference electrode exceeds −400 mV. Because the sum of absolute values of the both is the voltage difference at which the generation of hydrogen and oxygen by the electrolysis of water occurs between the working electrode and the counter electrode, it is found that, in the case of the sensor, the generation of hydrogen and oxygen by the electrolysis of water occurs at about 1600 mV.

Accordingly, when the potential of the working electrode to the potential of the reference electrode of the sensor is not more than −600 mV, the hydrogen can be generated on the working electrode.

From these results, it is confirmed by conducting the following tests that, without using the correction gas including the carbon monoxide components, the correction or/and deterioration judgement of the sensor can be electrically conducted from the outside.

From the normal measurement condition in which the potential of the working electrode whose reference is the reference electrode, is kept between about 0 to −300 mV, the potential is lowered to −600 mV for a predetermined time, and hydrogen is generated, and after a predetermined time (standing time), the condition is returned again to the measurement condition, and the sensor output value at that time is converted to the concentration of carbon monoxide gas (hydrogen gas concentration) according to the characteristics shown in FIG. 3. The result is shown in the following Table 1.

TABLE 1

| hydrogen generation time (sec) | measurement waiting time (min) | sensor output ($\mu$A) | concentration equivalent to carbon monoxide (ppm) |
| --- | --- | --- | --- |
| 1.0 | 1 | 23.0 | 958 |
| 1.0 | 2 | 10.2 | 425 |
| 1.0 | 3 | 3.9 | 162 |
| 1.0 | 5 | 0.8 | 33 |
| 2.0 | 3 | 20.5 | 854 |
| 2.0 | 5 | 6.4 | 267 |
| 0.5 | 1 | 10.8 | 450 |
| 0.5 | 3 | 0.3 | 12 |

From Table 1, by controlling the hydrogen generation time and standing time, it is found that the sensor response in the wide concentration equivalent to carbon monoxide (concentration of hydrogen) can be obtained. Accordingly, when it is desired to confirm the condition of the sensor in the vicinity of the necessary gas concentration, by setting an arbitrary hydrogen generation time and an arbitrary standing time, the deterioration condition, or the like, of the sensor in the vicinity of the necessary concentration can be grasped. Accordingly, when the hydrogen generation time and the measurement waiting time are appropriately selected, the correction corresponding to various carbon monoxide concentration can be conducted.

In order to confirm this, a carbon monoxide gas sensor is prepared, and when the hydrogen generation time is set to 1 sec., and the standing time is set to 2 min., the concentration equivalent to carbon monoxide is 425 ppm, as shown in Table 1, and this is defined as the reference value. Then, the sensor is deteriorated, and the concentration equivalent to the carbon monoxide, which is converted from the sensor output at the same generation time and standing time of the sensor, is 200 ppm. Naturally, 425 ppm or the value near the value should be obtained, however, it is shown that, because the responsibility is lowered by the deterioration, the value does not coincide with the value of 425 ppm.

The correction value which is a ratio of the two, is 200/425=0.4706, and as described above, because the concentration of the carbon monoxide and the concentration of hydrogen have the relationship of 1 to 1, when the concentration of carbon monoxide is measured by this deteriorated sensor and 180 ppm is obtained, the corrected concentration of carbon monoxide is 180/0.4706=382.5 ppm.

INDUSTRIAL APPLICABILITY

As described above, according to the present invention, only by periodically applying the voltage from the outside, the correction and deterioration judgement of the electrochemical carbon monoxide can be carried out, and it is not necessary that the correction gas including carbon monoxide is made to practically flow to the sensor and the correction operation is carried out, and without being accompanied by a possibility that the correction service man is exposed to the carbon monoxide gas for correction, the correction operation is periodically carried out easily and simply.

Further, the periodical sensor correction or testing can be carried out by the electric signals from the outside, and when the concentration of the carbon monoxide in the circumstance is increased practically, and a possibility of poisoning is generated, a possibility that the sensor is not normally operated and alarm is not given, can be greatly decreased.

Accordingly, the present invention can greatly attribute to the industry.

What is claimed is:

1. A method for testing an electrochemical gas sensor, wherein the electrochemical gas sensor includes a working electrode which electrochemically oxidizes or reduces a first gas component to be detected, a counter electrode which causes an electrochemical reduction reaction or oxidation reaction corresponding to an oxidized or reduced amount of the first gas component, and an electrolyte, and wherein a sensor output, which is a value of an oxidation current or reduction current of the first gas component, is calculated and a concentration of the first gas component is detected, comprising the steps of:

applying a voltage in which the current flows in the reverse direction to the oxidation current or reduction current of the first gas component, between the working electrode and the counter electrode from an outside of the electrochemical gas sensor, so that the working electrode operates as a negative electrode and the counter electrode operates as a positive electrode; and after a second gas component is generated on the working electrode so as to be a predetermined concentration by the electrolysis of the electrolyte, measuring the sensor output which is a value of the oxidation current or reduction current on the working electrode of the second gas component, wherein a normal operation of the electrochemical gas sensor is determined if the second gas component has a sensor output substantially proportional to the sensor output of the first gas component in a concentration corresponding to the concentration of the first gas component.

2. The testing method of an electrochemical gas sensor described in claim 1, wherein the sensor is tested by using a correction value which is a ratio of the output of the measuring sensor in the predetermined concentration of the second gas component, and the sensor output calculated according to a reference value from the predetermined concentration of the second gas component.

3. The testing method of an electrochemical gas sensor described in claim 1, wherein the sensor is tested by using a correction value which is a ratio of the second gas component concentration calculated according to a reference value from the measuring sensor output, and the predetermined concentration of the second gas component.

4. The testing method of an electrochemical gas sensor described in claim 1, wherein the first gas component is carbon monoxide.

5. The testing method of an electrochemical gas sensor described in claim 4, wherein the electrolyte is an aqueous solution, and the second gas component is hydrogen.

6. A control apparatus of the electrochemical gas sensor wherein a testing means according to the testing method described in claim 4, is provided.

7. The testing method of an electrochemical gas sensor described in claim 1, wherein the testing is correction, and/or deterioration judgement, and/or life judgement.

8. An electrochemical gas sensor, wherein a testing means according to the testing method described in claim 7, is provided.

9. An apparatus wherein an electrochemical gas sensor, and a testing means according to the testing method described in claim 7, are provided.

* * * * *